United States Patent [19]

Miyazawa et al.

[11] Patent Number: 5,557,016

[45] Date of Patent: Sep. 17, 1996

[54] PROCESS FOR PRODUCING ALKADIENOLS

[75] Inventors: Chihiro Miyazawa, Tokyo; Tomoyuki Mori, Kurashiki; Hiroshi Kameo, Kurashiki; Shinji Isogai, Kurashiki, all of Japan

[73] Assignee: Mitsubishi Kasei Corporation, Tokyo, Japan

[21] Appl. No.: 196,180

[22] PCT Filed: Jun. 29, 1993

[86] PCT No.: PCT/JP93/00891

§ 371 Date: Apr. 6, 1994

§ 102(e) Date: Apr. 6, 1994

[87] PCT Pub. No.: WO94/00410

PCT Pub. Date: Jan. 6, 1994

[30] Foreign Application Priority Data

Jun. 30, 1992 [JP] Japan ..................................... 4-173154

[51] Int. Cl.$^6$ .................................................. C07C 33/02
[52] U.S. Cl. .......................................................... 568/909.5
[58] Field of Search ............................................ 568/909.5

[56] References Cited

U.S. PATENT DOCUMENTS 3,670,032 6/1972 Romanelli .
3,992,456 11/1976 Atkins et al. .
4,356,333 10/1982 Yoshimura et al. .
4,417,079 11/1983 Yoshimura et al. .
4,511,437 4/1985 Heck et al. .

FOREIGN PATENT DOCUMENTS

| 4223363 | 2/1993 | Germany . |
| 54-144307 | 10/1979 | Japan . |
| 54-144306 | 10/1979 | Japan . |
| 56-145235 | 11/1981 | Japan . |
| 57-123129 | 7/1982 | Japan . |
| 57-134427 | 8/1982 | Japan . |
| 58-85828 | 5/1983 | Japan . |
| 64-25738 | 1/1989 | Japan . |

*Primary Examiner*—Rebecca Cook
*Attorney, Agent, or Firm*—Nixon & Vanderhye

[57] ABSTRACT

The disclosure describes a process for producing alkadienols comprising the steps of: reacting a conjugated alkadiene with water in a reaction solvent in the presence of a palladium catalyst; distilling the obtained reaction mixture so as to separate the reaction solvent from the reaction mixture while directly supplying heated water, steam or a mixture thereof as a heating medium to a distillation column, under the condition that the temperature of a bottom liquid in the distillation column is not higher than 120° C.; and phase-separating bottoms discharged from the bottom of the distillation column.

6 Claims, 1 Drawing Sheet

PROCESS FOR PRODUCING ALKADIENOLS

This is a continuation of PCT/JP93/0089, filed Jun. 9, 1993, and published as WO94/00410 Jan. 6, 1994.

TECHNICAL FIELD

The present invention relates to a process for producing alkadienols and, more particularly, to a process for producing alkadienols comprising the steps of: reacting a conjugated alkadiene with water in the presence of a palladium catalyst; distilling and separating the obtained reaction mixture; and phase-separating bottoms discharged from a distillation column so as to obtain the alkadienols which are a dimerized hydrate of the conjugated alkadiene.

BACKGROUND ART

Alkadienols, especially, octadienol is a chemical industrially important compound as an intermediate for producing n-octanol and an ester or the like thereof.

As a method of producing alkadienols, a method of reacting a conjugated alkadiene with water in the presence of a catalyst composed of a palladium compound and a phosphine or a phosphite, and carbon dioxide is conventionally known.

For example, Japanese Patent Application Laid-Open (KOKAI) No. 54-144306 discloses a process for producing 2,7-octadiene-1-ol comprising a hydration and dimerization step for producing octadienol by reacting 1,3-butadiene with water in the presence of a catalyst composed of a nonaqueous palladium compound and a phosphine or a phosphite, carbon dioxide and an organic solvent; a low-boiling point component separation step for separating a low-boiling point by-product, water and the organic solvent from the liquid reaction product (reaction mixture) obtained in the hydration and dimerization step so as to obtain a component containing octadienol, a high-boiling point by-product and the catalyst; a flash distillation step for flash-distilling the obtained component containing octadienol, the high-boiling point by-product and the catalyst so as to separate a fraction containing octadienol from a high-boiling point component containing the high-boiling point by-product and the catalyst; a catalyst recovery step for separating the high-boiling point by-product from the high-boiling point component so as to obtain a catalyst solution; and an octadienol refining step for distilling the obtained fraction containing octadienol so as to separate 1,7-octadiene-3-ol and a high-boiling point ingredient, thereby refining 2,7-octadiene-1-ol.

It is described that the low-boiling point by-product separation step in the above-mentioned process is carried out at a temperature of not higher than 110° C. in order to remove 1,3,7-octadiene which is a by-product and the low-boiling point solvent such as acetone, from the reaction mixture. It is also described that a remaining liquid in the distillation still is composed of an organic phase and an aqueous phase, and that the aqueous phase separated from the remaining liquid is recycled to the hydration and demerization step.

In the low-boiling point component separation step for separating a low-boiling point component from the reaction mixture, if the distilling temperature is too high, for example, if it exceeds 120° C. the alkadienols produced is decomposed and/or polymerized so that the yield is reduced, and the palladium catalyst is metallized. Such a loss in the alkadienols and the palladium catalyst is not only caused by the high distillation temperature but also influenced by the method of supplying the heat which is necessary for the distillation.

The heat necessary for distillation is generally indirectly supplied to a bottom liquid in the distillation column through a heat exchanger such as a shell-type kettle, a tubular-type kettle and a jacketed-type kettle. In such a heat supply system (indirect heating system), since the bottom liquid is heated by passing a heating medium heated to a temperature generally at least 30° C. higher than the temperature of the bottom liquid, through the heat exchanger, the temperature of the heating surface of the heat exchanger which is in contact with the bottom liquid in the distillation column is higher than the temperature of the bottom liquid. For example, the temperature of the transfer surface becomes not lower than 120° C. Therefore, in the case of the indirect heating, it is difficult to prevent the decomposition and/or polymerization of the alkadienols, and the metallization of the palladium catalyst due to the local heating by the heating surface of the heat exchanger, so that the loss in the alkadienols and the palladium catalyst is very large.

That is, although the method disclosed in Japanese Patent Application Laid-Open (KOKAI) No. 54-144306 is advantageous in that the temperature of the bottom liquid in the distillation column can be restricted because water exists in the bottom liquid, it is disadvantageous in that since the distillation and separation in the low-boiling point component separation step is carried out by the indirect heating, there is a loss in the alkadienols and the palladium catalyst due to the local heating by the heating surface of the heat exchanger.

As a result of studies undertaken by the present inventors so as to solve the above-described problem, it has been found that in the process for producing alkadienols comprising the steps of: reacting a conjugated alkadiene with water in a reaction solvent in the presence of a palladium catalyst; distilling the obtained reaction mixture so as to separate the reaction solvent from the reaction mixture; and phase-separating bottoms discharged from the bottom of a distillation column, when the reaction mixture is distilled under the condition that the temperature of the bottom liquid in the distillation column is not higher than 120° C. while directly supplying heated water and/or steam as a heating medium to the distillation column, the alkadienols is not decomposed nor polymerized and the palladium catalyst is not metallized, so that there is hardly any loss in the alkadienols and the palladium catalyst.

DISCLOSURE OF THE INVENTION

The present invention has been made on the basis of this finding. It is an object of the present invention to provide an improved process for producing alkadienols by reacting a conjugated alkadiene with water in a reaction solvent in the presence of a palladium catalyst, which facilitates the separation of the reaction solvent from the obtained reaction mixture without a loss in the alkadienols and the palladium catalyst. It is another object of the present invention to provide an industrially advantageous process for producing alkadienols.

To achieve these aims, in a first aspect of the present invention, there is provided (1) a process for producing alkadienols comprising the steps of: reacting a conjugated alkadiene with water in a reaction solvent in the presence of a palladium catalyst; distilling the obtained reaction mixture so as to separate the reaction solvent from the reaction mixture, while directly supplying heated water, steam or a mixture thereof as a heating medium to a distillation column, under the condition that the temperature of a bottom liquid in the distillation column is not higher than 120° C.; and phase-separating bottoms discharged from the distillation column.

In a second aspect of the present invention there is provided (2) a process for producing alkadienols comprising the steps of: reacting a conjugated alkadiene with water in a reaction solvent having a lower boiling point than water, in the presence of a palladium catalyst; distilling the obtained reaction mixture so as to separate the low-boiling point reaction solvent from the reaction mixture under the condition that the temperature of the bottom liquid in the distillation column is not higher than 120° C.; and phase-separating bottoms discharged from the distillation column, wherein during the distillation process, at least a part of the aqueous solution of the aqueous phase obtained by the phase separation of the bottoms is heated and returned as a heating medium to the distillation column, so that sufficient water for the phase separation of the bottoms at ordinary temperature is kept in the bottom liquid in the distillation column.

In a third aspect of the present invention there is provided (3) a process for producing alkadienols comprising the steps of: reacting a conjugated alkadiene with water in a water-soluble low-boiling point reaction solvent in the presence of a palladium catalyst; supplying the obtained reaction mixture to a middle plate in a distillation column and distilling the reaction mixture under the conditions that the rate of the aqueous phase in the bottom liquid in the distillation column is 20 to 98 wt %, the temperature of the bottom liquid is 30° to 120° C., and the pressure in the distillation column is 0.1 to 2 atm; and phase-separating bottoms discharged from the distillation column, wherein during the distillation process, a heating medium composed of the heated water and steam produced by heating at least a part of the aqueous solution of the aqueous phase obtained by the phase separation of the bottoms is directly introduced into the bottom liquid in the distillation column.

The present invention will be explained in detail in the following.

As the conjugated alkadiene which is able to produce alkadienols by reacting with water, 1,3-butadiene, 2-ethyl-1,3-butadiene, 2,3-dimethyl-1,3-butadiene, isoprene, 1,3-pentadiene, chloroprene, 1,3-octadiene, etc. are usable.

When 1,3-butadiene is used as a starting material, examples of the starting material which is generally easily available, are commercial refined 1,3-butadienes, so-called a BBP (butane-butadiene product) such as a $C_4$ fraction mixture in the naphtha decomposition product.

When the BBP is used as a starting material, it is preferable to separate and remove in advance the acetylenes and the allenes contained in the BBP. The total concentration of the acetylenes and the allenes in the 1,3-butadienes as a starting material is preferably as low as possible. Generally, the total concentration is preferably about not more than 1.0 wt % based on 1,3-butadienes. A method of reducing the acetylenes and the allenes is not restricted and a known method can be appropriately adopted.

As water used as the other starting material, water having a purity of a degree which does not influence the hydration and dimerization is appropriately used. The amount of water is not restricted, but it is generally selected from the range of 0.5 to 10 mol, preferably 1 to 5 mol based on one mole of the conjugated alkadiene.

In order to maintain the temperature of the bottom portion of the distillation column at a temperature not higher than a predetermined temperature, namely, not higher than 120° C. in the distillation and separation process which will be described later, it is preferably to use a larger amount of water than that which is necessary for the hydration and dimerization.

The form and the valence of the palladium compound used as the palladium catalyst in the present invention are not necessarily restricted. As examples of the palladium compound may be cited metallic palladiums such as palladium black and a palladium metal with a carrier; O-valent palladium complexes such as bis (t-butylisonitrile) palladium (O), bis(t-amylisonitrile) palladium (O), bis (cyclohexylisonitrile) palladium (O), bis(phenylisonitrile) palladium (O), bis(p-tolylisonitrile) palladium (O), bis(2,6-dimethylphenylisonitrile) palladium (O), tris (dibenzylideneacetone) dipalladium (O), (1,5-cyclooctadiene) (maleic anhydride) palladium (O), bis(norbornene) (maleic anhydride) palladium (O), bis(maleic anhydride) (norbornene) palladium (O), (dibenzylideneacetone) (bipyridyl) palladium (O), and (p-benzoquinone) (o-phenanthroline) palladium (O); tetrakis(phosphine) palladium complexes, tris (phosphine) palladium complexes, and bis (phosphine) palladium complexes which have a phosphine compound as a ligand such as tetrakis (triphenylphosphine) palladium (O), tris(triphenylphosphine) palladium (O), bis-(tritolylphosphine) palladium (O), bis(trixylyl) palladium (O), bis(trimesitylphosphine) palladium (O), bis(tritetramethylphenyl) palladium (O) and bis(trimethylmethoxyphenylphosphine) palladium (O), and tetrakis (phosphite) palladium complexes, tris (phosphite) palladium complexes, and bis (phosphite) palladium complexes which have a phosphite compound as a ligand and which correspond to the above-mentioned phosphine compounds; palladium inorganic salts such as palladium chloride (II), palladium nitrate (II), tetraammine dichloropalladium (II) and disodium tetrachloropalladium (II); palladium carboxylates such as palladium acetate (II), palladium benzoate (II) and palladium α-picolinate (II); palladium chelate compounds such as bis(acetylacetone) palladium (II) and bis(8-oxyquinoline) palladium (II); and divalent palladium complexes such as bis(allyl) palladium (II), (η-allyl) (η-cyclopentadienyl) palladium (II), (η-cyclopentadienyl) (1,5-cyclooctadiene) palladium (II) tetrafluoroborate, bis(benzonitrile) palladium (II) acetate, di-µ-chlorodichlorobis (t riphenylphosphine) dipalladium (II), bis(tri-n-butylphosphine) palladium (II) acetate and 2,2-bipyridyl palladium (II) acetate.

Among these, tetrakis(triphenylphosphine) palladium (O), bis(tritolylphosphine) palladium (O), bis(trixylyl) palladium (O), bis (trimethylmethoxyphenylphosphine) palladium (O), palladium acetate (II) and bis(acetylacetone) palladium (II) are preferable.

The amount of palladium compound used is ordinarily appropriately selected from the range of 0.00001 to 1 gram atom, preferably 0.0001 to 0.5 gram atom (as calculated in terms of a palladium atom) based on one mol of a conjugated alkadiene.

It is possible to use phosphines or phosphites as a co-catalyst together with a palladium compound. Examples of a phosphine or a phosphite used as the co-catalyst can be cited trialkyl phosphines such as tri-n-octylphosphine, tributylphosphine and dimethyl-n-octylphosphine and phosphites corresponding thereto; tricycloalkylphosphines such as tricyclohexyl phosphine; triarylphosphines such as triphenylphosphine, tritolylphosphine, diphenyl-p-chlorophenylphosphine, tris(p-methoxylphenyl) phosphine, di (tolyl) (phenyl) phosphine, (tolyl) di (phenyl) phosphine, tri (ethylphenyl) phosphine, di (ethylphenyl) (phenyl) phosphine, (ethylphenyl) di(phenyl) phosphine, tri(xylyl) phosphine, tri(mesityl) phosphine and tri(tetramethylphenyl) phosphine, and phosphites corresponding thereto; tertiary alkylarylphosphines such as diphenylethylphosphine, dimethylphenylphosphine, bis (diphenylphosphino) methane and 1,2-bis(diphenylphosphno) ethane, and phosphites corresponding thereto; alkoxyarylphosphines such as diethoxyphenylphosphine, ethoxydiphenylphosphine, dimethoxyphenylphosphine, diisopropoxyphenylphosphine, bis(2-butoxy) phenylphosphine and tri(methylmethoxyphenyl) phosphine, aryloxyalkylphosphines such as diphenoxyethylphosphine; phosphines containing a hetero atom such as diethylaminopropyldiphenylphosphine, morpholinopropyldiphenylphosphine and ethylsulfonylethyldiphenylphosphine.

Among these, hydrophobic phosphines such as triphenylphosphine, tri (tolyl) phosphine, di (tolyl) (phenyl) phosphine, (tolyl) di (phenyl) phosphine, tri (ethylphenyl) phosphine, di(ethylphenyl) (phenyl) phosphine, (ethylphenyl) di(phenyl) phosphine, tri(xylyl) phosphine, tri(mesityl) phosphine, tri(tetramethylphenyl) phosphine, and tri(methylmethoxyphenyl) phosphine are preferable.

Water-soluble phosphines represented by the following formula (I) are also usable:

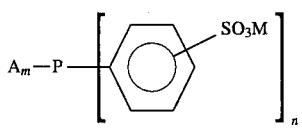

wherein A represents a phenyl group, M represents an alkali metal, m is an integer of 0 to 2, n is an integer of 1 to 3, and m+n=3.

In addition, cyclic phosphites represented by the following formula (II) or (III) are also usable:

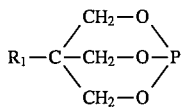

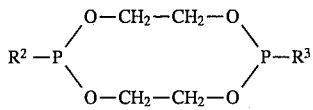

wherein $R^1$, $R^2$, and $R^3$ each represent an alkyl group such as methyl, ethyl and nonyl; an aryl group such as phenyl, tolyl and naphtyl; a hydroxyalkyl group such as hydroxymethyl, hydroxyethyl and hydroxypentyl; an alkoxyalkyl group such as ethoxymethyl; an aryloxyalkyl group such as phenoxymethyl; or an acyloxyalkyl group such as acetoxymethyl and acetoxypentyl. The amount of phosphines or phosphites used is ordinarily about 0.1 to 100 mol, preferably 0.1 to 10 mol based on one g of palladium, but it is not always restricted thereto.

As will be described later, when bottoms discharged from the bottom portion of the distillation column is separated into an aqueous phase and an organic phase, and at least a part of the aqueous solution in the aqueous phase is heated and returned to the distillation column, it is advantageous to use a hydrophobic phosphine as the co-catalyst. The reaction solvent having a lower boiling point than that of water is preferably used from the point of view of the selection of the distilling conditions and the efficiency in the separation of the reaction solvent, but a solvent having a higher boiling point than that of water or a solvent which forms an azeotrope with water is also usable. Examples of a solvent having a lower boiling point than water are ethers such as diethyl ether, tetrahydrofuran and ethylene glycol dimethyl ether; ketones such as acetone, methyl ethyl ketone; alkols such as methanol, ethanol, n-propanol, i-propanol and t-butanol; alkanes such as pentane, hexane and heptane; alkenes such as hexene. Examples of a solvent which forms an azeotrope with water are dioxane, trioxane, n-butyl alcohol, i-butyl alcohol, t-amyl alcohol, butyl acetate, butyl butyrate, toluene, xylene and butyl ether.

For the purpose of smooth reaction and smooth distillation and separation which will be described later, use of a water-soluble low-boiling point solvent which can dissolve at least partially both a conjugated diene and water, such as ethers, ketones and alcohols are preferable. Among these, tetrahydrofuran, acetone and t-butanol are especially preferably used.

The reaction temperature can be selected from a wide range of room temperature to about 180° C., but 50° to 130° C. is preferable, and 60° to 100° C. is more preferable. The reaction pressure can be selected from a wide range of ordinary pressure to about 200 kg/cm², but 3 to 70 kg/cm² is preferable. At the time of reaction, $CO_2$ gas may coexist in the reaction system as described in Japanese Patent Application Laid-Open (KOKAI) No. 50-10565, and an inert gas such as helium and argon may also coexist in the reaction system.

The reaction mixture contains a low-boiling point by-product such as alkatrienes, a high-boiling point by-product such as dialkadienyl ether, an organic carboxylic acid and an ester as well as the catalyst, the reaction solvent, unreacted water and conjugated alkadiene and alkadienols as the main product. The contents of the low-boiling point by-product and the high-boiling point by-product depend on the reaction conditions, but each of them is ordinarily about several mol % to several ten mol % based on the conjugated alkadiene.

In the present invention, as a distillation apparatus for distilling the reaction mixture, separating the reaction solvent from the reaction mixture and recovering alkadienols, a batch distillation apparatus is usable, but a continuous distillation apparatus is ordinarily used. The type of column may be any of a packed column, a bubble tower column, a perforated-plate column, etc. Among these, a packed column is industrially advantageously used.

It is essential in the present invention to distill the reaction mixture so as to separate the reaction solvent from the reaction mixture, under the condition that the temperature of the bottom liquid in the distillation column is not higher than 120° C., while directly supplying heated water and/or steam as a heating medium to the distillation column.

As the heating medium, the heated water having a temperature of not lower than 30° C. and/or steam having a temperature in the range of the boiling point under the operating pressure of the distillation column to 120° C. is preferably used. Furthermore, it is preferable to heat at least a part of the aqueous solution of the aqueous phase which is obtained by the later-described phase separation of the bottoms, to not lower than 30° C. and to return the heated solution to the distillation column. Especially, when at least a part of the aqueous solution of the aqueous phase which is obtained by the phase separation of the bottoms is supplied to the distillation column through a heat exchanger (heater), a part thereof is preferably converted into steam. The amount of steam is preferably in the range of 3 to 95 wt % based on the amount of water supplied to the heat exchanger. Although the heated water and/or the steam as the heating medium may be supplied to a position other than the bottom portion of the distillation column so long as it can be utilized as a heat source for the distillation column, it is ordinarily supplied to the bottom portion of the distillation column.

By using heated water and/or steam as a heating medium and directly introducing to the distillation column, it is possible to prevent the decomposition and/or the polymerization of the alkadienols and the metallization of the palladium catalyst caused by the local heating of the heating surface due to indirect heating using a heat exchanger or the like.

By directly introducing a heating medium produced by heating at least a part of the aqueous solution of the aqueous phase which is obtained by the phase separation of the bottoms, to the distillation column, it is possible not only to prevent the decomposition and/or the polymerization of the alkadienols and the metallization of the palladium catalyst but also to reduce the load for discharging the water after the distillation and the phase separation.

Especially by heating at least a part of the aqueous solution of the aqueous phase which is obtained by the phase separation of the bottoms so as to convert it to heated water and steam, and directly supplying to the distillation column, it is possible not only to prevent the decomposition and/or the polymerization of the alkadienols and the metallization of the palladium catalyst but also to reduce the load for discharging the water after the distillation and the phase separation. In addition, it is possible to prevent the heating surface for heating water obtained by the phase separation from being contaminated due to the adhesion of harzburgite and it is easy to heat the bottom liquid to a predetermined temperature with the steam.

In the present invention, the content of the aqueous phase of the bottoms (the rate of the aqueous phase separated to the whole) is adjusted to not less than 20 wt %, preferably 20 to 98 wt %, more preferably 30 to 97 wt %.

The distillation process in the present invention is carried out under the conditions that an aqueous phase exists in the bottom liquid in the distillation column and the temperature of the bottom liquid is not higher than 120° C. If the temperature of the bottom liquid exceeds 120° C., alkadienols as the target is sometimes decomposed and/or polymerized. The temperature of the bottom liquid in the distillation column is preferably 30° to 110° C., more preferably 50° to 105° C.

The distillation process in the present invention is also carried out under the condition that the pressure in the distillation column is not more than 2 atm, preferably 0.1 to 1.8 atm, more preferably 0.35 to 1.5 arm. When the distillation process is industrially carried out, if the pressure in the distillation column is too low, there is a problem of pressure reducing control or, when a low-boiling point solvent is used, there is a problem of the load for cooling the solvent so as to condense before recovery. Therefore, atmospheric distillation which does not require any special apparatus for pressure reduction or pressurization, is industrially advantageous.

The appropriate distilling conditions can be realized by appropriately selecting the conditions such as the position of a feed tray and the reflux ratio. When a solvent having a higher boiling point than that of water is used, it is possible to make the aqueous phase remain in the bottoms by extracting the solvent mainly from the top of the distillation column by, if necessary, an azeotropic distillation using a component which can form a low-boiling point azeotrope with the solvent.

The reaction mixture is preferably supplied to a middle plate in the distillation column. In other words, a predetermined number of plates are provided in the recovery portion under the feed tray in order that the water-soluble low-boiling point solvent does not exist substantially in the bottom liquid in the distillation column. The theoretical number of plates in the recovery portion is preferably not less than one when acetone is used as the water-soluble low-boiling point solvent; not less than two when tetrahydrofuran is used as the water-soluble low-boiling point solvent; and not less than three when t-butanol is used as the water-soluble low-boiling point solvent.

The supply of the reaction mixture to a middle plate in the distillation column enables the water-soluble low-boiling point solvent not to exist substantially in the bottom liquid in the distillation column. Therefore, it is possible to recover alkadienols from the bottoms by an easy and simple method such as phase separation. It is possible to reuse the solvent distilled and separated from the reaction mixture as a reaction solvent by recycling at least a part of the solvent to the reaction system.

The bottoms discharged from the distillation column is allowed to stand as it is if necessary after cooling, so as to separate an aqueous phase from an organic phase. At least a part of the aqueous phase which is obtained by the phase separation of the bottoms is heated by a heat exchanger such as a reboiler and returned to the distillation column by a recycling pump.

The aqueous phase in the present invention refers to a phase composed mainly of water, which does not form a homogeneous phase with a phase mainly composed of an organic layer and in which an organic or inorganic ingredient may be dissolved therein within the saturation solubility. The organic phase refers to a phase composed mainly of an organic ingredient such as alkadienols, which does not form a homogeneous phase with a phase mainly composed of water and in which water, the catalyst, etc. may be dissolved therein within the saturation solubility.

A preferred process of the present invention will now be explained with reference to FIG. 1.

In a reaction vessel 11, a conjugated alkadiene is reacted with water in a reaction solvent in the presence of a palladium catalyst, and the obtained reaction mixture is supplied to a reaction mixture storage tank 1. The reaction mixture is then supplied from the storage tank 1 to a middle plate in a distillation column 2, and distilled so as to be separated from the reaction solvent. The reaction solvent is extracted from the top portion of the distillation column 2 as a recovered solvent 3. A part of the recovered solvent 3 is returned to reaction vessel 11 as a recycle solvent 14. The effluent discharged from the bottom portion of the distillation column 2 is extracted as bottoms 12 and supplied to an oil/water separator (phase separator) 4. The bottoms 12 is separated into an aqueous phase and an organic phase by the oil/water separator 4, and the organic phase containing alkadienols is extracted from the oil/water separator 4 as a reaction product 6. The aqueous phase is also extracted from the oil/water separator 4 as an aqueous-phase effluent 13. A part of the aqueous-phase effluent 13 is heated by a heater 16 and returned to the distillation column 2 as a heated recycle solution 5 by a recycling pump 17. Although not shown in FIG. 1, a gas separation tank may be provided at the stage subsequent to the reaction vessel 11 so as to separate and recover the unreacted alkadiene and $CO_2$ gas and recycle them to the reaction vessel 11.

According to the process of the present invention, it is possible to separate and return a solvent with efficiency without losing a Pd catalyst and alkadienols and, hence, to produce alkadienols with high efficiency.

Figure 1:
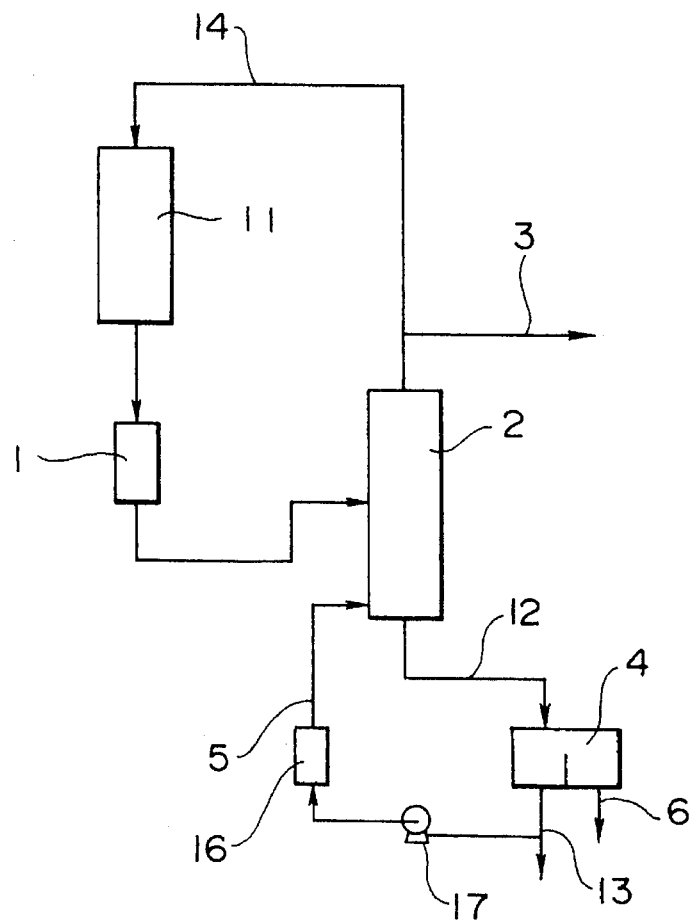
FIG. 1 schematically shows the process for producing alkadienols, which was carried out in Example 1.
Figure 2:
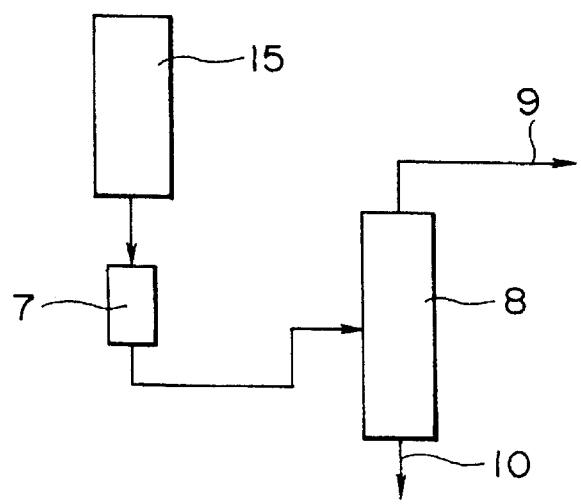
FIG. 2 schematically shows the process for producing alkadienols, which was carried out in Comparative Example 1.

The reference numerals in FIGS. 1 and 2 represent the following elements:

2 . . . distillation column, 4 . . . oil/water separator,
5 . . . heated recycle solution, 8 . . . distillation column
10 . . . bottoms, 11 . . . reaction vessel,
12 . . . bottoms, 15 . . . reaction vessel, 16 . . . heater,
17 . . . recycling pump.

BEST MODE FOR CONDUCTING THE INVENTION

The present invention will now be explained in more detail with reference to the following examples, but it is to be understood that the present invention is not restricted thereto and various modifications are possible within the scope of the invention.

EXAMPLE 1

1200 g of 1,3-butadiene, 260 g of water, 8.7 g of bis (acetylacetone) palladium, 30 g of triphenylphosphine and 3 liter of acetone were charged in a stainless steel electromagnetic rotary autoclave having an internal volume of 10 liter, and reacted at a temperature of 90° C. for 3 hours while elevating the pressure up to 20 kg/cm$_2$ G with $CO_2$ gas.

As shown in FIG. 1, the reaction mixture obtained was continuously supplied to the distillation column 2 at the rate shown in Table 1, and distilled under the conditions that the temperature of the top portion was 60° C., the temperature of the bottom portion was 101° C. and the operating pressure was 760 mmHg. The acetone as the solvent was completely distilled from the distillate extracting pipe at the top as the recover solvent 3, and an aqueous phase and an organic phase containing octadienol were discharged from the bottom of the distillation column as the bottoms 12. The distillation column 2 used was a perforated-plate column having 35 plates in actual number, and the eleventh plate from the top of the distillation column 2 was used as the feed tray (i.e, the recovery portion thereof had 25 plates). The reflux ratio was set at 0.5.

The bottoms 12 (the rate of the aqueous phase thereof: 98 wt %) was allowed to stand in the oil/water separator 4 for the purpose of phase separation, and the aqueous solution of the aqueous phase was heated to 102° C. by the heater 16. The heated aqueous solution was returned to the distillation column 2 as the heated recycle solution 5. The amount of heated recycle solution was 1,800 ml/Hr. The amount of steam produced by the heater 16 was 18 wt % based on the amount of water supplied to the heater 16. The reaction product 6 in the organic phase was analyzed by extracting from an organic phase extracting pipe by three samplings. Table 1 shows the amount of reaction mixture supplied to the distillation column 2, the concentration of each ingredient in the reaction mixture, the amount of sample (Sample Nos. 1-1 to 1-3) extracted from the organic phase extracting pipe and the concentration of each ingredient of the sample.

The recovery ratio of octadienol were 102%, 96% and 99%, respectively. The interior of the distillation column 2 was clean and no metallization of Pd was observed. The concentration of each ingredient was obtained from the analysis by gas chromatography.

EXAMPLE 2

Distillation was carried out in the same way as in Example 1 except that the temperature of the top portion of the distillation column was 35° C. the temperature of the bottom portion thereof was 78° C., the operating pressure was 300 mmHg and the aqueous solution of the aqueous phase which was heated to a temperature of 80° C. by the heater 16 and returned to the distillation column 2 as the heated recycle solution 5 was used as the heating medium. The distillation column 2 used was a perforated-plate column having 35 plates in actual number, and the eleventh plate from the top of the distillation column was used as the feed tray. The reflux ratio was set at 0.5. The composition of the reaction mixture is shown in Table 2. The content of the aqueous phase in the bottoms was 97 wt %. As a result of analysis of the organic phase after the phase separation by three samplings, the recovery ratio of octadienol were 99%, 99% and 98%, respectively. Table 2 shows the analyzed value of each ingredient. The interior of the distillation column was clean each time and no metallization of Pd was observed as in Example 1.

EXAMPLE 2

Distillation was carried out in the same way as in Example 1 except that 35 g of tri(o-tolyl) phosphine was used in place of 30 g of triphenylphosphine. The content of the aqueous phase in the bottoms was 97 wt %. As a result of analysis of the organic phase after the phase separation by sampling, the recovery ratio of octadienol was found to be 99%. Table 3 shows the analyzed value of each ingredient. The interior of the distillation column was clean and no metallization of Pd was observed as in Example 1.

EXAMPLES 4 TO 7

Distillation was carried out in the same way as in Example 1 except that the conditions were varied as shown in Table 4. Table 4 shows the composition of the reaction mixture, the rate of the aqueous phase in the bottoms, the composition of the organic phase after the phase separation, and the recovery ratio of octadienol. The interior of the distillation column was clean and no metallization of Pd was observed as in Example 1.

EXAMPLE 8

Distillation was carried out in the same way as in Example 1 except that water heated to 102° C. was supplied at a rate of 900 g/Hr in place of recycling the aqueous solution of the aqueous phase. Table 4 shows the composition of the reaction mixture, the rate of the aqueous phase in the bottoms, the composition of the organic phase after the phase separation, and the recovery ratio of octadienol. The interior of the distillation column was clean and no metallization of Pd was observed as in Example 1.

EXAMPLE 9

The reaction mixture obtained in the same way as in Example 1 was supplied to a stainless steel packed tower having an inner diameter of 40 mm and a height of 5,000 mm, and distillation was carried out in the same way as in Example 1. McMahon of 6 mm in diameter was used as the packing, and the H.E.T.P was 300 mm. The reaction mixture was supplied to a position of 1,300 mm from the bottom of the packed tower. After the bottoms was phase-separated, the aqueous solution of the aqueous phase was heated to a temperature of 100° C., and the heated solution was returned to the distillation column at the rate of 3,000 ml/Hr. The temperature of the top portion of the distillation column was 56° C., the temperature of the bottom portion thereof was 99° C. the operating pressure was 760 mmHg, and the rate of the aqueous phase in the bottoms was 90 wt %. As a result of analysis of the organic phase after the phase separation by sampling, the recovery ratio of octadienol was found to be 99%. Table 7 shows the analyzed value of each ingredient. The interior of the packed tower was clean and no metallization of Pd was observed as in Example 1

Comparative Example 1

1945 g of 1,3-butadiene, 865 g of water, 7.5 g of bis(acetylacetone) palladium, 25.8 g of triphenylphosphine and 2.3 liter of N,N-dimethylformamide were charged in a stainless steel electromagnetic rotary autoclave 15 having an internal volume of 10 liter, and reacted at a temperature of 90° C. for 3 hours while elevating the pressure up to 20 $kg/cm^2$ G with $CO_2$ gas.

As shown in FIG. 2, the reaction mixture obtained was continuously supplied to the distillation column 8 at the rate shown in Table 5, and distilled under the conditions that the temperature of the top portion of the distillation column was 100° C. the temperature of the bottom portion thereof was 160° C. and the operating pressure was atmospheric pressure, while indirectly heating the bottom portion of the distillation column by oil of 180 ° C. as a heating medium. A low-boiling point component 9 composed mainly of water and octadiene was distilled from the distillate extracting pipe at the top. The operating pressure was then changed to 1 mmHg, and distillation was carried out at a top temperature of 27° C. and a bottom temperature of 72° C. The N,N-dimethylformamide was distilled and the other components were discharged from the bottoms extracting pipe at the bottom portion as the bottoms 10.

The bottoms 10 was only an organic phase without any aqueous phase. A black deposit was observed in the organic phase and the interior of the distillation column blackened. As a result of analysis of the deposit by atomic absorption spectroscopy, it proved to be Pd. The bottoms 10 was sampled three times and mixed with the N,N-dimethylformamide distilled from the top. When the mixture was analyzed, the recovery ratio of octadienol were as low as 62%, 63% and 58%, respectively. Table 5 shows the analyzed values.

Comparative Example 2

Reaction was carried out in the same way as in Example 1. The reaction mixture obtained was distilled in the distilling apparatus shown in FIG. 2 under the conditions that the temperature of the top portion of the distillation column was 56° C., the temperature of the bottom portion thereof was 101° C. and the operating pressure was atmospheric pressure, while indirectly heating the bottom portion of the distillation column with oil of a temperature of 130° C. as a heating medium. Acetone was distilled from the top and an aqueous phase and an organic phase were discharged from the bottom portion of the distillation column.

After sampling and phase-separating the bottoms, the organic phase was analyzed to obtain the recovery of octadienol. The weight ratio of the organic phase and the aqueous phase was 94: 6. The analyzed value of each element is shown in Table 6. The recovery ratio of octadienol was only 70%. Pd was metallized in the bottom portion of the distillation column and a contamination looking like a black plated portion was observed.

INDUSTRIAL APPLICABILITY

A process according to the present invention does not cause the decomposition and/or polymerization of alkadienols nor the metallization of a palladium catalyst. Therefore, the loss in alkadienols and a palladium catalyst is suppressed, so that alkadienols as the target is produced with a high yield.

TABLE 1

| | | Reaction mixture | Sample No. 1-1 | Sample No. 1-2 | Sample No. 1-3 |
| --- | --- | --- | --- | --- | --- |
| Weight (g/Hr) | | 216.8 | 75.0 | 75.0 | 75.8 |
| Ingredient (wt %) | Octadienol | 18.1 | 53.4 | 50.2 | 51.3 |
| | Octatriene | 1.1 | 2.9 | 2.5 | 2.9 |
| | Dioctadienyl ether | 9.0 | 27.0 | 26.0 | 26.0 |

TABLE 2

| | | Reaction mixture | Sample No. 2-1 | Sample No. 2-2 | Sample No. 2-3 |
| --- | --- | --- | --- | --- | --- |
| Weight (g/Hr) | | 211.9 | 73.5 | 73.8 | 73.4 |
| Ingredient (wt %) | Octadienol | 20.7 | 59.1 | 58.8 | 58.6 |
| | Octatriene | 0.9 | 3.1 | 2.6 | 2.5 |
| | Dioctadienyl ether | 9.0 | 23.0 | 27.0 | 25.0 |

TABLE 3

| | | Reaction mixture | Composition of organic phase |
| --- | --- | --- | --- |
| Weight (g/Hr) | | 216.7 | 75.8 |
| Ingredient (wt %) | Octadienol | 21.6 | 61.1 |
| | Octatriene | 0.9 | 1.1 |
| | Dioctadienyl ether | 5.8 | 16.4 |

TABLE 4

| | Ex. 4 | Ex. 5 | Ex. 6 | Ex. 7 | Ex. 8 |
| --- | --- | --- | --- | --- | --- |
| Distilling condition | | | | | |
| Top temperature (°C.) | 32 | 94 | 56 | 56 | 63 |
| Bottom temperature (°C.) | 59 | 120 | 101 | 102 | 102 |
| Operating pressure (mmHg) | 100 | 1300 | 760 | 760 | 760 |
| Reaction mixture | | | | | |
| Weight (g/Hr) | 211.3 | 220.1 | 214.0 | 215.0 | 213.2 |
| Octadienol (Wt %) | 20.7 | 19.2 | 20.8 | 21.3 | 21.2 |
| Octatriene (wt %) | 0.9 | 1.0 | 0.8 | 0.9 | 1.1 |
| Dioctadienyl ether (wt %) | 3.5 | 2.6 | 2.3 | 2.1 | 3.3 |
| Organic phase | | | | | |
| Weight (g/Hr) | 63.5 | 63.8 | 60.1 | 60.8 | 63.3 |
| Octadienol (Wt %) | 67.5 | 63.6 | 74.8 | 76.8 | 71.2 |
| Octatriene (wt %) | 2.8 | 3.8 | 2.1 | 3.3 | 4.1 |
| Dioctadienyl ether (wt %) | 10.8 | 11.3 | 8.1 | 7.5 | 11.8 |
| Heating medium | | | | | |
| Amount of water | 20 | 1800 | 1800 | 900 | heated |

TABLE 4-continued

|  | Ex. 4 | Ex. 5 | Ex. 6 | Ex. 7 | Ex. 8 |
| --- | --- | --- | --- | --- | --- |
| recycled (ml/H) |  |  |  |  | water 900 (g/h) |
| Heating temperature (°C.) | 60 | 120 | 102 | 102 | 102 |
| Rate of aqueous phase in bottoms (wt %) | 30 | 96.3 | 97.0 | 93.0 | 93.0 |
| Recovery ratio of octadienol (%) | 98 | 96 | 101 | 102 | 100 |

TABLE 5

|  |  | Reaction mixture | Sample No. 3-1 | 3-2 | 3-3 |
| --- | --- | --- | --- | --- | --- |
| Weight (g/Hr) |  | 220.0 | 190 | 187 | 184 |
| Ingredient (wt %) | Octadienol | 31.6 | 22.7 | 23.4 | 21.9 |
|  | Octatriene | 0.3 | 0.02 | 0.02 | 0.01 |
|  | Dioctadienyl ether | 7.0 | 9.0 | 11.0 | 13.0 |

TABLE 6

|  |  | Reaction mixture | Composition of organic phase |
| --- | --- | --- | --- |
| Weight (g/Hr) |  | 211.2 | 75.3 |
| Ingredient (wt %) | Octadienol | 19.7 | 38.6 |
|  | Octatriene | 1.3 | 6.0 |
|  | Dioctadienyl ether | 8.2 | 35.7 |

TABLE 7

|  |  | Reaction mixture | Composition of organic phase |
| --- | --- | --- | --- |
| Weight (g/Hr) |  | 820.0 | 316.0 |
| Ingredient (wt %) | Octadienol | 22.3 | 57.3 |
|  | Octatriene | 1.2 | 3.1 |
|  | Dioctadienyl ether | 8.3 | 23.0 |

We claim:

1. A process for producing alkadienols comprising the steps of:
   (a) reacting a conjugated alkadiene with water in a reaction solvent in the presence of a palladium catalyst;
   (b) distilling the obtained reaction mixture to separate said reaction solvent from said reaction mixture and to collect the alkadienols in the bottom of the distillation column while directly supplying heated water, steam or a mixture thereof as a heating medium to the distillation column, wherein said heating medium is a recycle solution of heated water and steam produced by heating at least a part of the aqueous solution of the aqueous phase obtained by the phase separation of the bottoms and wherein the temperature of the bottom liquid in said distillation column is not higher than 120° C.; and
   (c) phase-separating bottoms discharged from said distillation column.

2. A process for producing alkadienols according to claim 1, wherein said reaction solvent is a water-soluble solvent having a lower boiling point than water and is selected from the group consisting of ethers, ketones, alcohols or a mixture thereof.

3. A process for producing alkadienols according to claim 2, wherein said reaction solvent is selected from the group consisting of acetone, tetrahydrofuran, t-butanol or a mixture thereof.

4. A process for producing alkadienols according to claim 1, wherein said reaction mixture is supplied to a middle plate in said distillation column so as to distill said reaction mixture in the state in which said reaction solvent does not exist substantially in said bottom liquid in said distillation column.

5. A process for producing alkadienols comprising the steps of:
   (a) reacting a conjugated alkadiene with water in a reaction solvent having a lower boiling point than water in the presence of a palladium catalyst;
   (b) distilling the obtained reaction mixture so as to separate the low-boiling point reaction solvent from said reaction mixture and to collect the alkadienols in the bottom of a distillation column, wherein the temperature of said bottom liquid in said distillation column is not higher than 120° C.; and
   (c) phase-separating bottoms discharged from said distillation column;
wherein, during the distillation process, at least a part of the aqueous solution of the aqueous phase obtained by the phase separation of said bottoms is heated and returned as a heating medium into said distillation column, so that sufficient water for the phase separation of said bottoms at ordinary temperature is kept in said bottom liquid in said distillation column.

6. A process for producing alkadienols comprising the steps of:
   (a) reacting a conjugated alkadiene with water in a water-soluble solvent having a lower boiling point than water in the presence of a palladium catalyst;
   (b) supplying the obtained reaction mixture to a middle plate in a distillation column and distilling said reaction mixture and collecting the alkadienols in a bottom of the distillation column wherein the content of the aqueous phase in the bottom liquid in said distillation column is 20 to 98 wt %, the temperature of the bottom liquid is 30° to 120° C., and the pressure in said distillation column is 0.1 to 2 atm; and
   (c) phase-separating bottoms discharged from said distillation column;
wherein, during the distillation process, a heating medium composed of the heated water and steam produced by heating at least a part of the aqueous solution of the aqueous phase obtained by the phase separation of said bottoms is directly introduced into said bottom liquid in said distillation column.

* * * * *